US008283274B2

(12) United States Patent
Cheng et al.

(10) Patent No.: US 8,283,274 B2
(45) Date of Patent: Oct. 9, 2012

(54) BINDERLESS ZEOLITIC ADSORBENTS, METHODS FOR PRODUCING BINDERLESS ZEOLITIC ADSORBENTS, AND PROCESSES FOR ADSORPTIVE SEPARATION OF PARA-XYLENE FROM MIXED XYLENES USING THE BINDERLESS ZEOLITIC ADSORBENTS

(75) Inventors: Linda Shi Cheng, Highland Park, IL (US); Jack Hurst, Mobile, AL (US)

(73) Assignee: UOP LLC, Des Plaines, IL (US)

( * ) Notice: Subject to any disclaimer, the term of this patent is extended or adjusted under 35 U.S.C. 154(b) by 477 days.

(21) Appl. No.: 12/505,654

(22) Filed: Jul. 20, 2009

(65) Prior Publication Data

US 2011/0011804 A1   Jan. 20, 2011

(51) Int. Cl.
*B01J 29/06* (2006.01)
(52) U.S. Cl. .................. 502/75; 502/60; 502/73; 502/79
(58) Field of Classification Search .................... 502/60, 502/73, 75, 79
See application file for complete search history.

(56) References Cited

U.S. PATENT DOCUMENTS

| | | | |
|---|---|---|---|
| 2,985,589 A | 5/1961 | Broughton | |
| 3,310,486 A | 3/1967 | Broughton | |
| 3,686,342 A | 8/1972 | Neuzil | |
| 4,058,586 A | 11/1977 | Chi et al. | |
| 4,381,256 A | 4/1983 | Hildebrandt | |
| 4,424,144 A | 1/1984 | Pryor et al. | |
| 4,603,040 A | 7/1986 | Kuznicki et al. | |
| 4,642,397 A | 2/1987 | Zinnen et al. | |
| 4,818,508 A | 4/1989 | Flank et al. | |
| 4,886,929 A | 12/1989 | Neuzil et al. | |
| 4,961,881 A | 10/1990 | Ou | |
| 5,026,531 A | 6/1991 | Tannous et al. | |
| 5,045,295 A | 9/1991 | Tannous et al. | |
| 5,403,800 A | 4/1995 | Beck et al. | |
| 6,410,815 B1 | 6/2002 | Plee | |
| 6,478,854 B1 | 11/2002 | Kotagiri et al. | |
| 6,537,348 B1 | 3/2003 | Hirano et al. | |
| 7,179,367 B2 | 2/2007 | Feng et al. | |
| 7,271,305 B2 | 9/2007 | Williams et al. | |
| 7,812,208 B2 | 10/2010 | Cheng | |
| 7,820,869 B2 | 10/2010 | Priegnitz | |
| 2005/0170947 A1 | 8/2005 | Plee | |
| 2006/0199989 A1 | 9/2006 | Frey | |
| 2008/0076952 A1 | 3/2008 | Kulprathipanja | |
| 2008/0149565 A1 | 6/2008 | Lee et al. | |
| 2008/0200742 A1 | 8/2008 | Doyle et al. | |
| 2009/0036723 A1 | 2/2009 | Ghosh et al. | |
| 2009/0326308 A1 | 12/2009 | Kulprathipanja | |
| 2009/0326311 A1 | 12/2009 | Cheng | |

FOREIGN PATENT DOCUMENTS

WO   2008-009845 A1   1/2008

OTHER PUBLICATIONS

Wang, D., et al., Development in preparation and application of binderless zeolite molecular sieves, Petrochemical Technology 36(10) 2007 p. 1061-1066 Beijing Research Institute of Chemical Industry.
Guo, Y.C., et al., Separation of p-xylene from C8 aromatics on binder-free hydrophobic adsorbent of MFI zeolite. I. Studies on static equilibrium, Microporous and Mesoporous Materials 39(1/2) 2000 p. 149-161.
Guo, G. Q., et al., Studies on static phase equilibrium for adsorption separation of C8 aromatics on binder-free hydrophobic adsorbent, Petrochemical Technology 30(1) 2001 p. 20-25.
Sun, H., et al., N-Paraffins adsorption with 5A zeolites: The effect of binder on adsorption equilibria, Separation and Purification Technology 64(1) 2008 p. 135-139 Elsevier.
Morbidelli, M., et al., Separation of xylenes on y zeolites in the vapor phase—2. Breakthrough and pulse curves and their interpretation, Ind. Eng. Chem., Process Des. Dev. (ISSN 0196-4305) V24 N.1 83-88 (Jan. 1985) American Chemical Society (ACS.
Kurup, A., et al., Optimal operation of an industrial-scale parex process for the recovery of p-xylene from a mixture of C8 aromatics, Industrial and Engineering Chemistry Research 44(15) 2005 p. 5703-5714 American Chemical Society.
Minceva, M., et al., Simulated moving bed reactor for isomerization and separation of p-xylene, Chemical Engineering Journal 140(1/3) 2008 p. 305-323 Elsevier.
Laroches, C.L., et al., Optimising paa-xylene production through absorbent design: A new SPX adsorbent for ELUXYLTM process, L 7th World Congress of Chemical Engineering, GLASGOW2005, incorporating the 5th European Congress of Chemical Engineering 2005 p. 187, 7th World Congress of Chemical Engineering, GLASGOW2005, incorporating the 5th European Congress of Chemical Engineering, 2005, Glasgow, Scotland Institute of Chemical Engineers.
High-efficiency adsorbent for increasing paraxylene at Yangzi Petrochemical Company, Source: China Petroleum Processing and Petrochemical Technology (3) 2007 p. 28 Research Institute of Petroleum Processing, SINOPEC.
High-efficiency adsorbent for increasing paraxylene at Yangzi Petrochemical Company, Source: China Petroleum Processing and Petrochemical Technology (3) 2007 p. 28 Research Institute of Petroleum Processing, SINOPEC.
Gomes, P.S., et al., Operation of an industrial SMB unit for p-xylene separation accounting for adsorbent ageing problems, 2007 AIChE Annual Meeting 2007 p. 1, 2007 AIChE Annual Meeting, 2007, Salt Lake City, UT American Institute of Chemical Engineers.
Kurup, A.S., et al., Comparative study of modified simulated moving bed systems at optimal conditions for the separation of ternary mixtures of xylene isomers, Ilndustrial and Engineering Chemistry Research 45(18) 2006 p. 6251-6265 American Chemical Society.

*Primary Examiner* — Elizabeth Wood
(74) *Attorney, Agent, or Firm* — Mark R Willis

(57) ABSTRACT

Binderless BaKX zeolitic adsorbents, methods for their production, and processes for their use in a liquid phase adsorptive separation process are provided. An adsorbent includes a binder-converted zeolite portion formed from x wt % kaolin clay binder and (100-x) wt % unconverted Zeolite X with a silica:alumina molar ratio of about 2.5. The kaolin clay binder is in the range of about 10 to about 20 wt %. Ba and K occupy cationic exchangeable sites within the adsorbent. K is in the range of about 0.25 to about 0.9% by weight and Ba is greater than about 31.6% by weight of the binderless BaKX zeolitic adsorbent. Cornstarch may be added to the Zeolite X and kaolin clay binder to increase adsorbent macro-porosity and pore volume. Productivity of the adsorbent is improved decreasing process operating costs. The mechanical strength of the adsorbent is also improved.

10 Claims, 8 Drawing Sheets

HOLD VALUES : CORNSTARCH : 5.0

BINDERLESS ZEOLITIC ADSORBENTS, METHODS FOR PRODUCING BINDERLESS ZEOLITIC ADSORBENTS, AND PROCESSES FOR ADSORPTIVE SEPARATION OF PARA-XYLENE FROM MIXED XYLENES USING THE BINDERLESS ZEOLITIC ADSORBENTS

FIELD OF THE INVENTION

The present invention generally relates to zeolitic adsorbents, methods for production thereof, and methods for use thereof in an adsorptive separation process, and more particularly relates to binderless BaKX zeolitic adsorbents, methods for their production, and methods of recovering para-xylene from mixed xylenes in liquid-phase simulated moving bed adsorption processes using binderless BaKX zeolitic adsorbents.

DESCRIPTION OF RELATED ART

The simulated moving bed (SMB) adsorption process is used commercially in a number of large scale petrochemical separations to recover high purity para-xylene (PX) from mixed xylenes. As used herein, "mixed xylenes" refers to a mixture of $C_8$ aromatic isomers that includes ethyl benzene (EB), para-xylene (p-xylene or PX), meta-xylene (MX) and ortho-xylene (OX). High purity para-xylene is used for the production of polyester fibers, resins and films. Para-xylene typically is converted to terephthalic acid (TPA) or dimethyl terephthalate (DMT), which is then reacted with ethylene glycol to form polyethylene terephthalate (PET), the raw material for most polyesters.

The general technique employed in the performance of simulated moving bed adsorptive separation processes is widely described and practiced. Generally, the process simulates a moving bed of adsorbent with continuous countercurrent flow of a liquid feed over the adsorbent. Feed and products enter and leave adsorbent beds continuously, at nearly constant compositions. Separation is accomplished by exploiting the differences in affinity of the adsorbent for para-xylene relative to the other $C_8$ aromatic isomers.

Typical adsorbents used in simulated moving bed adsorption processes generally include crystalline aluminosilicate zeolites and can comprise both the natural and synthetic aluminosilicates. Suitable crystalline aluminosilicate zeolites for use as an adsorbent selective for para-xylene include those having aluminosilicate cage structures in which alumina and silica tetrahedra are intimately connected with each other in an open three dimensional crystalline network. The tetrahedra are cross linked by the sharing of oxygen atoms, with spaces between the tetrahedra occupied by water molecules prior to partial or total dehydration of the zeolite. The dehydration results in crystals interlaced with channels having molecular dimensions. In a hydrated form the crystalline aluminosilicate zeolites are generally represented by the formula: $M_{2/n}O:Al_2O_3:wSiO_2:yH_2O$ where "M" is a cation that balances the electrovalence of the tetrahedra and is generally referred to as an exchangeable cationic site, "n" represents the valence of the cation, "w" represents the moles of $SiO_2$, and "y" represents the moles of water. Such crystalline aluminosilicate zeolites that find use as an adsorbent possess relatively well-defined pore structures. The exact type aluminosilicate zeolite is generally identified by the particular silica: alumina molar ratio and the pore dimensions of the cage structures.

Cations (M) occupying exchangeable cationic sites in the zeolitic adsorbent may be replaced with other cations by ion exchange methods well known to those having ordinary skill in the field of crystalline aluminosilicates. Crystalline aluminosilicates, such as Zeolite X with barium and potassium cations at the exchangeable cationic sites within the zeolite, are known to selectively adsorb para-xylene in a mixture comprising at least one other $C_8$ aromatic isomer.

Generally, zeolitic adsorbents used in separative processes contain the zeolitic crystalline material dispersed in an amorphous material or inorganic matrix, having channels and cavities therein which enable liquid access to the crystalline material. Silica, alumina or certain clays and mixtures thereof are typical of such inorganic matrix materials, which act as a "binder" to form or agglomerate the zeolitic crystalline particles that otherwise would comprise a fine powder. Agglomerated zeolitic adsorbents may thus be in the form of particles such as extrudates, aggregates, tablets, macrospheres such as beads, granules, or the like.

The binder is typically inert and does not contribute to any adsorption. Efforts have been made to improve adsorbent productivity by increasing the selective part (zeolite volume) within adsorbents by converting the binder into selective zeolite in a conversion process referred to as "zeolitization", while maintaining the strength and macroporosity of the zeolitic adsorbent. This conversion process results in a "binderless" zeolitic adsorbent. While this conversion process has resulted in an increase in adsorbent productivity, still further increases in process performance and decreases in operating costs for adsorptive separation processes are sought.

Accordingly, it is desirable to provide a binderless adsorbent and methods to recover high purity para-xylene from mixed xylenes in a liquid-phase separation process using the binderless adsorbent so that process performance is improved and operating costs are lowered. In addition, it is desirable to provide a binderless BaKX zeolitic adsorbent that decreases the amount of adsorbent and desorbent required to process a fixed amount of feed and that has an increased meso- and macro-porosity, mass transfer rate, and mechanical strength. It is also desirable to provide a method for forming such a binderless adsorbent. Furthermore, other desirable features and characteristics of the present invention will become apparent from the subsequent detailed description of the invention and the appended claims, taken in conjunction with the accompanying drawings and this background of the invention.

SUMMARY OF THE INVENTION

The present invention provides a binderless BaKX zeolitic adsorbent, a method for producing the binderless BaKX zeolitic adsorbent, and a process for adsorptive separation of para-xylene from mixed xylenes using the binderless BaKX zeolitic adsorbent. The binderless BaKX zeolitic adsorbent comprises:

a binder-converted zeolite portion formed from x weight percent (wt %) inert clay binder, wherein x is in the range of about 10 wt % to about 20 wt % of the binderless BaKX zeolitic adsorbent;

(100-x) wt % zeolite X with a silica:alumina molar ratio of 2.5±0.5; and

Barium (Ba) and potassium (K) cations at cationic exchangeable sites within the binderless BaKX zeolitic adsorbent, wherein K is in the range of about 0.25 to about 0.9% by weight and the Ba is greater than about 31.6% by weight of the binderless BaKX zeolitic adsorbent. The binder-converted zeolite portion and Zeolite X may be mixed with cornstarch prior to formation of the binder-converted zeolite portion. The cornstarch comprises about 0 to about 5 weight percent of the combined wt % of the binder-converted zeolite portion and the Zeolite X. The weight percentages of Zeolite X, inert clay binder, cornstarch, K, and Ba are on a volatile-free basis.

In accordance with an exemplary embodiment, a method for producing an agglomerated binderless BaKX zeolitic adsorbent comprises forming agglomerates having ion-exchangeable sites, the agglomerates formed from Zeolite X with a silica:alumina molar ratio of about 2.5±0.5, and inert binder. Cornstarch may also be added during the agglomerate forming step. The agglomerates are then activated, during which step the cornstarch burns off. The activation step converts the kaolin clay binder to meta-kaolin clay binder. In the next step, the meta-kaolin clay binder is converted into binder-converted zeolite. The ion-exchangeable sites of the agglomerates are then exchanged with Ba and K wherein K is in the range of about 0.25 to about 0.9% by weight and the Ba greater than about 31.6% by weight of the agglomerated binderless BaKX zeolitic adsorbent. The agglomerated binderless BaKX zeolitic adsorbent is then dried to fix the water content thereof.

A process for separating para-xylene from a mixture of aromatic xylenes comprises contacting the mixture with a binderless BaKX zeolitic adsorbent comprised of a Zeolite X portion having a silica to alumina molar ratio of 2.5±0.5 and a binder-converted zeolite portion, the binderless BaKX zeolitic adsorbent containing Ba and K at cationic exchangeable sites in weight %, respectively, of at least about 31.6% and about 0.25 to about 0.9% of the binderless BaKX zeolitic adsorbent. Para-xylene is selectively adsorbed on the adsorbent and the less selectively adsorbed portion of the mixture is removed from the process by means of a raffinate stream. The para-xylene is purified in a purification zone. The para-xylene is recovered by desorption with a desorbent in a desorption zone and recovered by an extract stream.

BRIEF DESCRIPTION OF THE DRAWINGS

The present invention will hereinafter be described in conjunction with the following drawing figures, wherein like numerals denote like elements, and wherein.

DETAILED DESCRIPTION

The following detailed description of the invention is merely exemplary in nature and is not intended to limit the invention or the application and uses of the invention. Furthermore, there is no intention to be bound by any theory presented in the preceding background of the invention or the following detailed description of the invention.

In accordance with exemplary embodiments of the present invention, a binderless BaKX zeolitic adsorbent comprises a binder-converted zeolite portion formed from x weight percent (wt %) inert clay binder, wherein x is in the range of about 10 wt % to about 20 wt % of the binderless BaKX zeolitic adsorbent, and (100-x) wt % Zeolite X (a crystalline aluminosilicate zeolite) with a silica:alumina molar ratio of 2.5±0.5. Ba and K are at cationic exchangeable sites within the binderless BaKX zeolitic adsorbent, with the K in the range of about 0.25 to about 0.9% by weight and the Ba greater than about 31.6% by weight of the binderless BaKX zeolitic adsorbent. Further, the inert clay binder and the Zeolite X may be mixed with cornstarch prior to formation of the binder-converted zeolite portion. The cornstarch comprises about 0 to about 5 wt % of the combined wt % of the binder-converted zeolite portion and the Zeolite X. The weight percentages of Zeolite X, inert clay binder, cornstarch, K, and Ba are on a volatile-free basis. The pore volume of the binderless BaKX zeolitic adsorbent measured by Hg intrusion porosimetry is between about 0.25 cc/g and 0.35 cc/g.

According to exemplary embodiments of the present invention, Zeolite X comprises a specific crystalline aluminosilicate zeolite for use in the adsorbent. In hydrated form, Zeolite X can be represented in terms of mole oxides as follows:

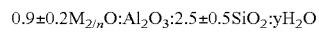

$$0.9\pm0.2 M_{2/n}O:Al_2O_3:2.5\pm0.5 SiO_2:yH_2O$$

where "M" is at least one cation having a valence of not more than 3, which balances the electrovalence of the tetrahedra and is generally referred to as an exchangeable cationic site, "n" represents the valence of the cation, and "y" represents the moles of water (y is a value up to about 9 depending upon the identity of M and the degree of hydration of the crystalline). Zeolite X possesses a relatively well-defined pore structure. As the Zeolite X is initially prepared, the cation "M" is usually predominantly sodium and thus is referred to as a sodium-type Zeolite X. The defined $SiO_2/Al_2O_3$ mole ratio of Zeolite X is in the range of about 2.5±0.5. In a preferred embodiment, the Zeolite X has a silica:alumina molar ratio in the range of about 2.3 to about 2.7, and most preferably is about 2.5.

Figure 1:
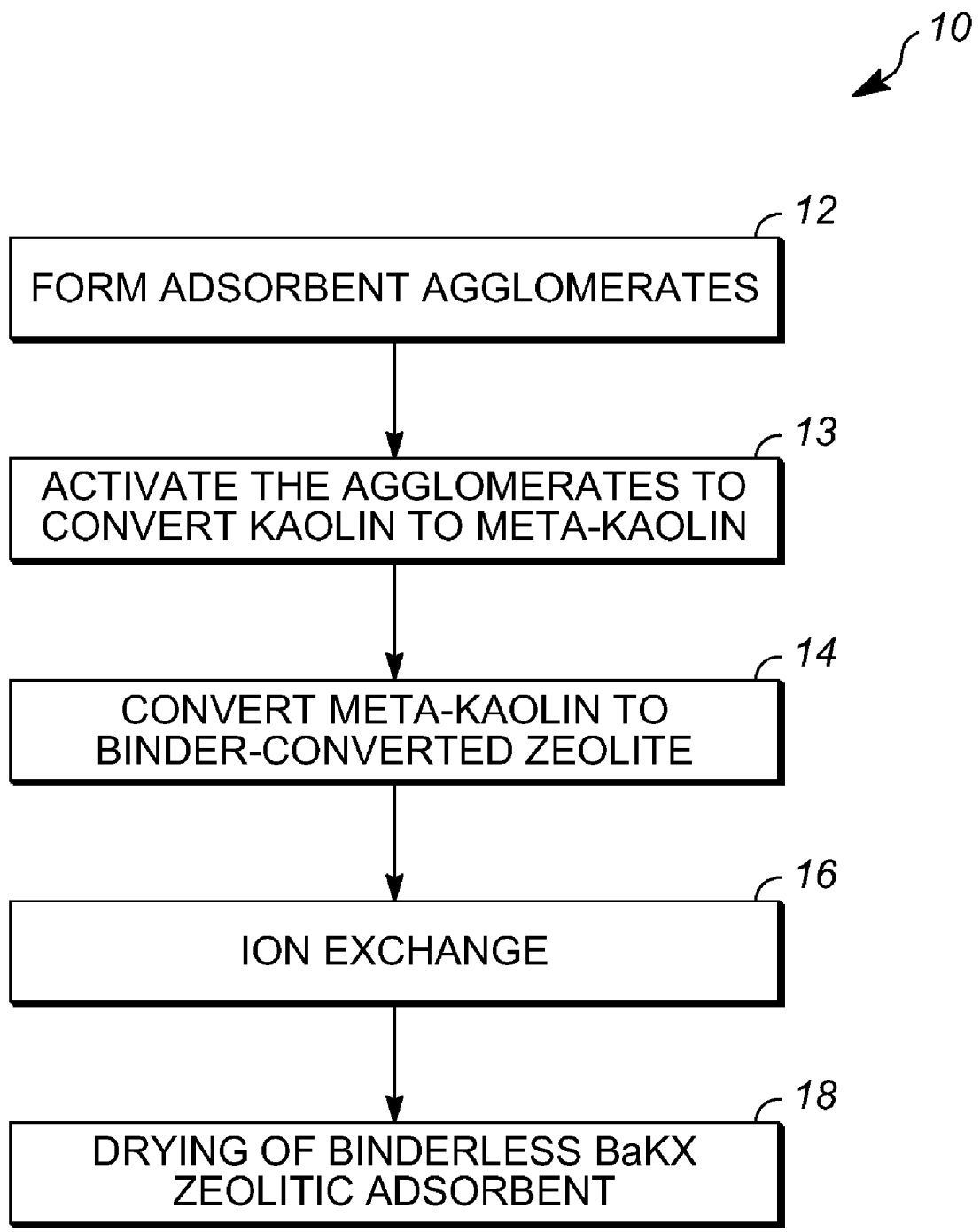
FIG. 1 is a flow chart of methods of producing a binderless BaKX zeolitic adsorbent according to exemplary embodiments of the present invention.

FIG. 1 is a flow chart of a method 10 for preparing the binderless BaKX zeolitic adsorbent in accordance with an exemplary embodiment. The method begins with the formation of adsorbent agglomerates (step 12) comprised of the Zeolite X and inert binder. The Zeolite X is agglomerated into adsorbent beads using the inert binder by mixing at ambient temperature with water. In a preferred embodiment, the inert binder comprises kaolin clay with a silica:alumina molar ratio in the range of about 2.0 to about 2.2, preferably about 2.0. Kaolin clay is available from U.S. Silica Co., Berkeley Springs, W. Va., for example. The beads may be comprised of from about 80 to about 90 wt % of Zeolite X and about 10 to about 20 wt % of kaolin clay binder (on a volatile-free basis). The kaolin clay binder holds the starting zeolite powder together to form adsorbent beads with a particle size in the range of about 0.3 mm to about 0.8 mm and having increased mechanical strength as shown by water attrition tests as hereinafter described. While agglomerates in the form of beads have been described, the invention is not so limited. The Zeolite X may be agglomerated into other forms of particles such as extrudates, aggregates, tablets, macrospheres, granules, or the like.

In an exemplary embodiment, additives, such as cornstarch, may also be mixed with the Zeolite X and inert binder during the agglomerate-forming step 12. Cornstarch may be added in an amount from about 0 to about 5.0 wt % (on a volatile-free basis) of the total combined weight of the binder-converted zeolite portion and the starting Zeolite X for purposes as hereinafter described. Other additives may include polymers and fibers.

To convert the kaolin clay binder to a binder-converted zeolite, the agglomerates are activated at about 625° C. or higher to convert the kaolin clay binder into meta-kaolin clay binder (step 13). The kaolin clay binder undergoes an endothermic dehydroxylation reaction and converts to a disordered meta-kaolin phase. If cornstarch was previously added, it burns off during this step.

Next, the meta-kaolin clay binder is then caustic-digested at a temperature of about 80° C. by a sodium hydroxide solution and the meta-kaolin binder is converted to binder-converted zeolite having a silica:alumina molar ratio in the range of from about 2.0 to about 2.2, preferably about 2.0 (step 14). For 1 g of meta-kaolin clay binder, 41 g of 2.4 wt % NaOH is needed for conversion. The conversion results in about a 15% increase in selective pore volume as determined through McBain $O_2$ capacity measurements at liquid $O_2$ temperature. Such measurement is described in "Zeolite Molecular Sieves: Structure, Chemistry and Use" by Donald W. Breck, John Wiley & Sons, 1974. Thus, the adsorbent beads comprise substantially 100% zeolite with negligible inert binder, forming "binderless" zeolitic adsorbent beads. The adsorbent beads comprise a Zeolite X portion (from the starting Zeolite X) with a silica:alumina molar ratio in the range of about 2.5±0.5, preferably about 2.5, and the binder-converted zeolite portion with a silica:alumina molar ratio in the range of about 2.0 to about 2.2, preferably about 2.0. While the conversion of a kaolin clay binder to binder-converted zeolite has been described, the invention is not so limited. For example, other clay binders may be converted to a binder-converted zeolite. Non-limiting examples include clays belonging to the halloysite family. In addition, while the use of a sodium hydroxide solution has been described as the caustic solution for binder conversion, the invention is not so limited. In addition to sodium hydroxide, other aqueous alkali metal hydroxide solutions may be used for conversion. Non-limiting examples include a solution of potassium hydroxide or a mixture of sodium hydroxide and potassium hydroxide The binderless zeolitic adsorbent beads are then exposed to $Ba^{2+}$ cations and $K^+$ cations for ion-exchange to produce the "binderless BaKX zeolitic adsorbent" (step 16). In a preferred embodiment, substantially all of the ion-exchangeable Na sites of the binderless zeolitic adsorbent beads are exchanged with Ba and K such that the weight percent of Na in the binderless BaKX zeolitic adsorbent preferably is less than about 0.3%, most preferably less than about 0.11% (on a volatile free basis). The barium and potassium ions are exchanged in relative amounts so that K is in the range of about 0.25 to about 0.9% by weight on a volatile free basis (not including water), preferably about 0.3 to about 0.75% by weight and the Ba is greater than about 31.6% by weight of the binderless BaKX zeolitic adsorbent.

In one exemplary embodiment, the exchange can be in a single step with a mixture of Ba and K such that the weight percentages of Ba and K in the binderless BaKX zeolitic adsorbent will be in the above-mentioned ranges. Alternatively, the exchanges may take place sequentially, with each step exchanging an appropriate amount of ions to produce a binderless BaKX zeolitic adsorbent having weight percentages of Ba and K ions in the above-described ranges. The single step and alternative sequential step exchange are identified collectively in FIG. 1 as step 16. While the ion exchange is described as occurring after agglomeration of the Zeolite X and after conversion, the invention is not so limited. The exchange with Ba and K may occur prior to agglomeration of the Zeolite X or after forming agglomerates and before conversion, but some ion exchange after conversion may still be required as sodium hydroxide is used to convert the meta-kaolin to zeolite. Cation exchange capacity calculations in Zeolite X are described in "Zeolite Molecular Sieves: Structure, Chemistry, and Use" by Donald W. Breck, John Wiley & Sons, 1974.

Next, the binderless BaKX zeolitic adsorbent is dried to fix its water content (step 18). In this regard, the binderless BaKX zeolitic adsorbent is activated by washing and drying the beads to about 4 to about 7% Loss on Ignition (LOI at 900° C.). The drying is generally carried out by thermal activation, preferably at temperatures of from about 175° C. to about 250° Celsius. The water content of the adsorbent is expressed herein in terms of the recognized LOI test at 900° C. The LOI test is described in UOP Test Method No. UOP954-03 (available through ASTM International, 100 Barr Harbor Drive, PO Box C700, West Conshohocken, Pa., 19428-2959 USA).

As noted above, cornstarch may be added to the Zeolite X and the clay binder mixture during the bead-forming stage. The addition of cornstarch increases the meso- and macro-porosity of the adsorbent beads, as explained in more detail below. As used herein and conventionally, "macro-pores" are defined as pores having a pore diameter greater than 50 nm and "meso-pores" are defined as pores having a pore diameter between 2 and 50 nm. Macro- and meso-porosity facilitates conversion of the binder by permitting the sodium hydroxide conversion solution to flow throughout the binder. The macro- and meso-pores also help improve the mass transfer rate of the binderless BaKX zeolitic adsorbent.

Figure 10:
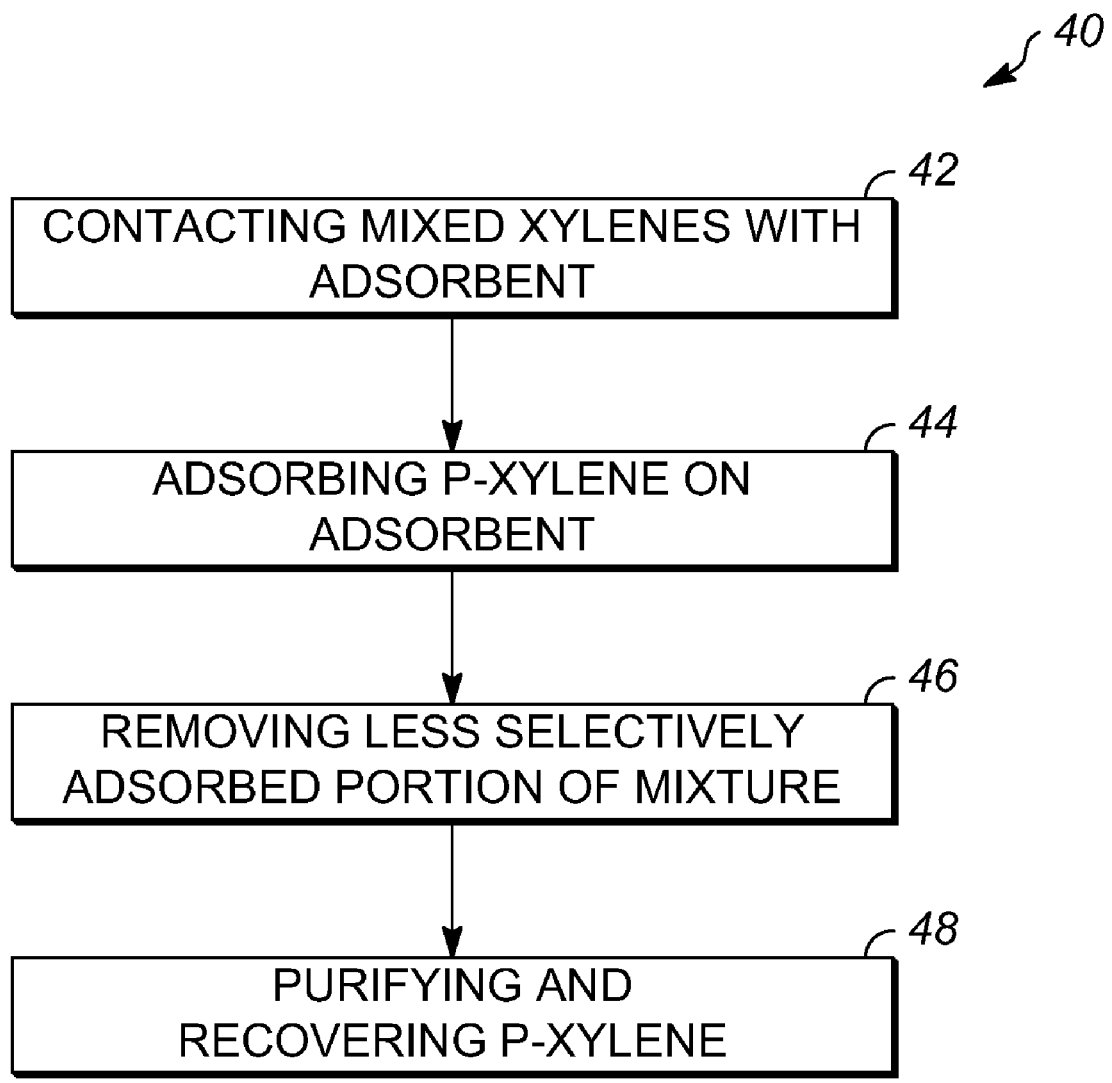
FIG. 10 is a flow chart illustrating the process steps for use of the binderless BaKX zeolitic adsorbent in the adsorptive separation unit of FIG. 2 in accordance with exemplary embodiments of the present invention.

The binderless BaKX zeolitic adsorbents, according to exemplary embodiments of the present invention, may be used in a simulating moving bed adsorptive separation process for the recovery of para-xylene from mixed xylenes. The adsorbents are selective for para-xylene. In one exemplary embodiment as shown in FIG. 10, the process 40 comprises contacting the mixture xylenes at liquid phase adsorption conditions with a binderless BaKX zeolitic adsorbent (step 42), causing para-xylene to be adsorbed on the binderless BaKX zeolitic adsorbent (step 44), causing a less selectively adsorbed portion of the mixture to be removed from contact with the binderless BaKX adsorbent by means of a raffinate stream (step 46), and purifying and recovering the para-xylene by desorption with a desorbent at desorption conditions (step 48). The desorbent displaces the para-xylene from the adsorbent. Adsorption conditions can include a temperature range of from about 148° Celsius to about 177° Celsius (300 degrees Fahrenheit to about 350 degrees Fahrenheit), and a pressure range of from about atmospheric to about 3447 KPa (500 psig) as required to ensure liquid phase operations, with pressures of about 690 kPa (100 psig) being preferred (herein referred to as "liquid phase adsorption conditions"). Preferred cycle times are 20-34 minutes. Desorption conditions preferably include the same temperature and pressure as used for adsorption.

Figure 2:
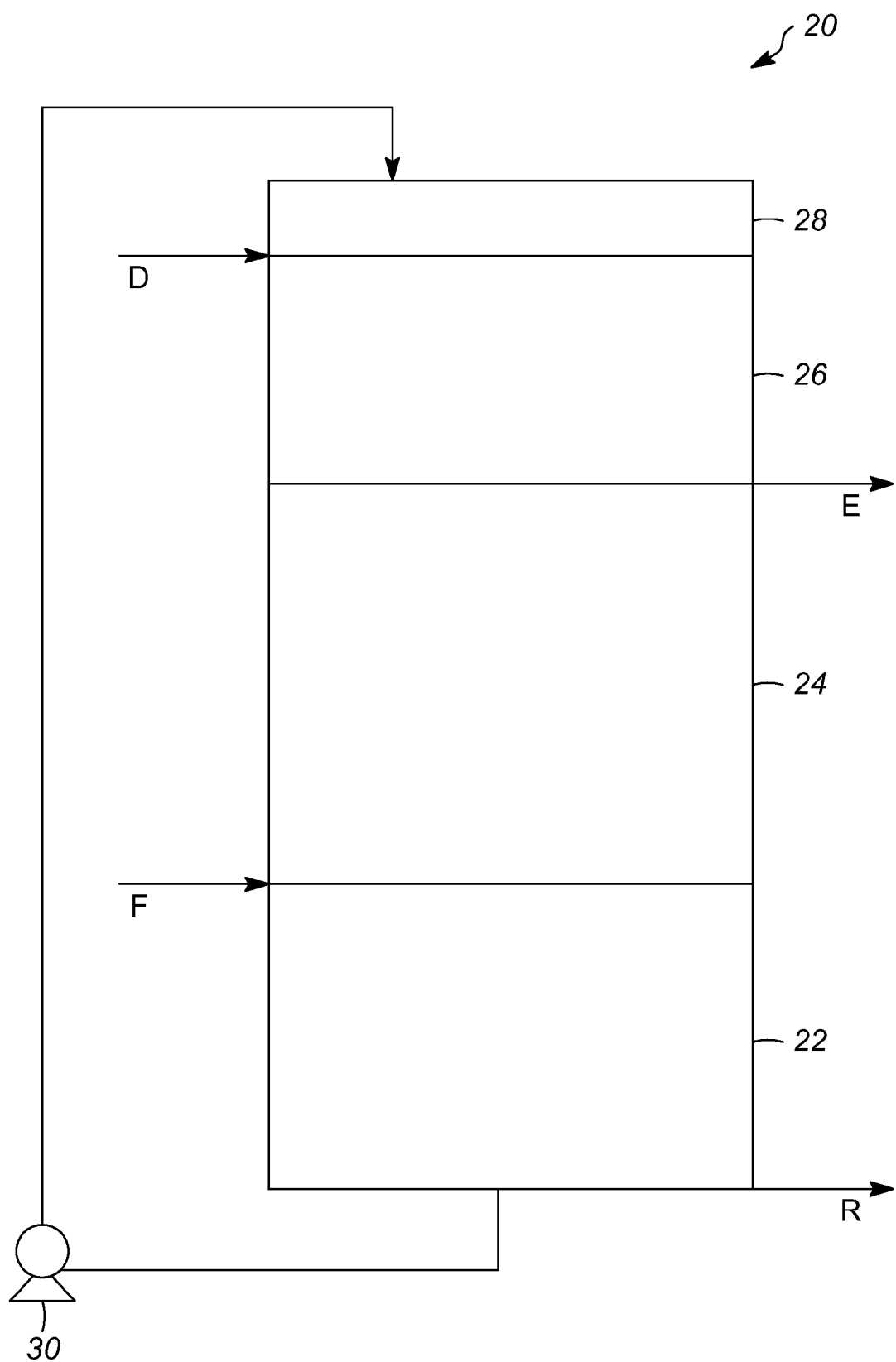
FIG. 2 is a simplified illustration of an exemplary four zone adsorbent chamber of an adsorptive separation unit used in the process of FIG. 1 according to an exemplary embodiment of the present invention.

In the simulated moving bed adsorptive separation process, these steps are performed in separate zones (as hereinafter described) within adsorbent beads retained in one or more adsorption chambers. FIG. 2 shows a simplified four-zone adsorbent chamber 20. In the simulated moving bed adsorptive separation process 40, the adsorption and displacement are continuously taking place using the continuous flow of feed F and desorbent streams D and allows continuous production of an extract E and a raffinate stream R. In such a system, it is the progressive movement of multiple liquid access points down an adsorbent chamber that simulates the upward movement of adsorbent contained in the adsorbent chamber 20.

A number of specially defined terms are used in describing the simulated moving bed processes. The term "feed stream" or "feed inlet stream" indicates a stream in the process through which a feed mixture passes to the adsorbent. The feed mixture comprises one or more extract components and one or more raffinate components. An "extract component" is a compound or type of compound that is more selectively retained by the adsorbent while a "raffinate component" or "raffinate material" is a compound or type of compound that is less selectively retained. Here, the feed mixture comprises mixed xylenes. As stated previously, as used herein "mixed xylenes" refers to a mixture of $C_8$ aromatic isomers that includes ethyl benzene (EB), para-xylene (PX), meta-xylene (MX) and ortho-xylene (OX). Accordingly, ethyl benzene (EB) and meta- and ortho-xylene (MX and OX, respectively) from the feed stream are raffinate components while para-xylene (PX) is the extract component. The term "desorbent" shall mean generally a material capable of displacing an extract component. A suitable desorbent for the process described herein comprises p-diethylbenzene (PDEB), but the invention is not so limited Other suitable desorbents include toluene and tetralin. The term "desorbent stream" or "desorbent inlet stream" indicates the stream through which desorbent passes to the adsorbent. The term "raffinate stream" or "raffinate outlet stream" means a stream through which most of the raffinate components are removed from the adsorbent. The composition of the raffinate stream can vary from about 100% desorbent to essentially 100% raffinate components. The term "extract stream" or "extract outlet stream" shall mean a stream through which an extract material, which has been displaced by desorbent, is removed from the adsorbent. The composition of the extract stream can vary from about 100% desorbent to essentially 100% extract components.

The term "selective pore volume" of the adsorbent is defined as the volume of the adsorbent which selectively retains extract components from the feed stream. The term "non-selective void volume" of the adsorbent is the volume of the adsorbent that does not selectively retain extract components from the feed stream. This volume includes the cavities of the adsorbent, which are capable of retaining raffinate components, and the interstitial void spaces between adsorbent particles. The selective pore volume and the non-selective void volume are generally expressed in volumetric quantities and are of importance in determining the proper flow rates of fluid required to be passed into an operational zone for efficient operations to take place for a given quantity of adsorbent.

When adsorbent "passes" into an operational zone (hereinafter defined and described) its non-selective void volume together with its selective pore volume carries fluid into that zone. The non-selective void volume is utilized in determining the amount of fluid that should pass into the same zone in a countercurrent direction to the adsorbent to displace the fluid present in the non-selective void volume. If the fluid flow rate passing into a zone is smaller than the non-selective void volume rate of adsorbent material passing into that zone, there is a net entrainment of liquid into the zone by the adsorbent. Since this net entrainment is a fluid present in a non-selective void volume of the adsorbent, in most instances, it comprises less selectively retained feed components.

In the simulated moving bed process, four liquid access points are active at any one time: the feed inlet stream, desorbent inlet stream, raffinate outlet stream, and extract outlet stream access lines. Additional access lines may be used as needed. Coincident with this simulated upward movement of the solid adsorbent is the movement of the liquid occupying the void volume of the adsorbent. So that countercurrent contact is maintained, a liquid flow down the adsorbent chamber may be provided by a pump. As an active liquid access point moves through a cycle, that is, from the top of the adsorbent chamber to the bottom, the chamber circulation pump 30 moves through different zones which require different flow rates. A programmed flow controller (not shown) may be provided to set and regulate these flow rates.

The active liquid access points effectively divide the adsorbent chamber into separate zones, each of which has a different function. In this embodiment of the process, three separate operational zones typically are present in order for the process to take place, although in some instances an optional fourth zone may be used.

Referring to FIG. 2, an adsorption zone 22 is defined as the adsorbent located between the feed inlet stream and the raffinate outlet stream. In this zone, the feed stream contacts the adsorbent, an extract component is retained, and a raffinate stream is withdrawn. Since the general flow through zone 22 is from the feed stream which passes into the zone to the raffinate stream which passes out of the zone, the flow in this zone is considered to be in a downstream direction when proceeding from the feed inlet to the raffinate outlet streams.

Immediately upstream with respect to fluid flow in adsorption zone 22 is a purification zone 24. The purification zone 24 is defined as the adsorbent between the extract outlet stream and the feed inlet stream. The basic operations taking place in zone 24 are the displacement from the non-selective void volume of the adsorbent of any raffinate component carried into zone 24 by the shifting of adsorbent into this zone and the displacement of any raffinate component retained within the selective pore volume of the adsorbent. Purification is achieved by passing a portion of extract stream material leaving a desorption zone 26 (discussed hereinafter) into zone 24 at the zone 24 upstream boundary to effect the displacement of raffinate material. The flow of liquid in zone 24 is in a downstream direction from the extract outlet stream to the feed inlet stream. The para-xylene is further enriched as the desorbent pushes the raffinate components from the non-selective void volume of the adsorbent and the selective void volume into zone 22.

Immediately upstream of zone 24 with respect to the fluid flowing in zone 24 is the desorption zone 26. The desorption zone 26 is defined as the adsorbent between the desorbent inlet and the extract outlet streams. The function of the desorption zone 26 is to allow a desorbent which passes into this zone to displace the extract component which was retained in the adsorbent during a previous contact with the feed stream in zone 22 in a prior cycle of operation. The flow of fluid in zone 26 is essentially in the same direction as that of zones 22 and 24.

In an optional exemplary embodiment, a buffer zone, zone 28, may be utilized. This zone, defined as the adsorbent between the raffinate outlet stream and the desorbent inlet stream, if used, is located immediately upstream with respect to the fluid flow to zone 26. Zone 28 can be utilized to conserve the amount of desorbent utilized in the desorption step since a portion of the raffinate stream which is removed from zone 22 can be passed directly into zone 28 to displace present desorbent and cause it to flow to the desorption zone 26. Zone 28 contains enough desorbent so that raffinate material present in the raffinate stream passing from zone 22 into zone 28 can be prevented from passing into zone 26, thereby contaminating the extract stream removed from zone 24. In the instances in which optional zone 28 is not utilized, the raffinate stream flowing from zone 22 to zone 28 must be carefully monitored so that the flow directly from zone 22 to zone 26 can be stopped when there is an appreciable quantity of raffinate material present in the raffinate stream passing from zone 22 into zone 26 to prevent the extract outlet stream from being contaminated.

EXAMPLES

The following are examples of binderless BaKX zeolitic adsorbents having various formulations (Formulations A-K), as shown in TABLE 1 below, in accordance with exemplary embodiments. The examples are provided for illustration purposes only, and are not meant to limit the various embodiments of the present invention in any way.

These examples were prepared according to the steps described above using 13X1 zeolite powder with a silica: alumina molar ratio of about 2.5 and kaolin clay binder.

TABLE 1

| Formulation | Zeolite, wt % | Kaolin clay binder, wt % | Cornstarch, wt % | K, wt % | Ba, wt % | Na, wt % |
|---|---|---|---|---|---|---|
| A | 82 | 18 | 0 | 0.3 | 32 | 0.1 |
| B | 88 | 12 | 0 | 0.3 | 32 | 0.2 |
| C | 82 | 18 | 5 | 0.3 | 33 | 0.1 |
| D | 88 | 12 | 5 | 0.3 | 33 | 0.1 |
| E | 82 | 18 | 0 | 1.0 | 32 | 0.2 |
| F | 88 | 12 | 0 | 1.0 | 32 | 0.1 |
| G | 82 | 18 | 5 | 1.0 | 32 | 0.1 |
| H | 88 | 12 | 5 | 1.0 | 32 | 0.1 |
| I | 85 | 15 | 2.5 | 0.7 | 33 | 0.1 |
| J | 85 | 15 | 2.5 | 0.7 | 33 | 0.1 |
| K | 85 | 15 | 2.5 | 0.7 | 33 | 0.1 |

Pulse/dynamic performance evaluation experiments, known in the art, were conducted with a particular feed mixture to measure adsorptive capacity and selectivity of the various formulations. A dynamic testing apparatus consisting of an adsorbent chamber of approximately 70 cc volume having inlet and outlet portions at opposite ends of the chamber was employed. The chamber was contained within a temperature control means and, in addition, pressure control equipment was used to operate the chamber at a constant predetermined pressure. Chromatographic analysis equipment was attached to the outlet line of the chamber and used to analyze, "on-stream", the effluent stream leaving the adsorbent chamber.

A pulse test, performed using this apparatus and the following general procedure, was used to determine selectivities, mass transfer, and other data for the various adsorbent formulations. The adsorbent was filled to equilibrium with p-diethylbenzene by flowing the desorbent through the adsorbent chamber. At a convenient time, a pulse of feed containing known concentrations of a nonadsorbed paraffinic tracer (n-nonane) and of the particular aromatic isomers (PX, EB, MX, and OX) diluted in the desorbent was injected for a duration of several minutes. After injection, desorbent flow was resumed, and the tracer and the aromatic isomers were eluted as in a liquid-solid chromatographic operation. The effluent was analyzed by on-stream chromatographic equipment and traces of the envelopes of corresponding component peaks were developed (not shown). (Alternatively, effluent samples could have been collected periodically and later analyzed separately by gas chromatography.) The dynamic test (also known as a breakthrough test) was also performed to determine adsorption capacity, PX/PDEB selectivity, and mass transfer characteristics. The adsorbent was first filled to equilibrium with toluene (containing a known concentration of a nonadsorbed paraffinic tracer (n-nonane) by flowing toluene through the adsorbent chamber. At a convenient time, the flow was switched to a mixture of para-xylene and para-diethylbenzene flow. Over time, para-xylene and para-diethylbenzene broke through. The adsorption capacity was determined by the difference in the total amount of para-xylene and para-diethylbenzene that was fed to the adsorbent chamber minus the total amount of para-xylene and paraethylbenzene that eluted.

From information derived from the chromatographic traces, adsorbent performance was rated in terms of capacity index for an extract component, and selectivity for one isomer with respect to another and to the desorbent. The higher the adsorbent's capacity for an extract component, the better is the adsorbent. Increased capacity of a particular adsorbent makes it possible to reduce the amount of adsorbent needed to separate the extract component for a particular charge rate of feed mixture. A reduction in the amount of adsorbent required for a specific adsorptive separation reduces the cost of the separation process. The good initial capacity of the adsorbent should be maintained during actual use in the separation process over some economically desirable life.

Selectivity (B) for an isomer can be expressed not only for one feed mixture component as compared to another, but can also be expressed between any feed mixture component and the desorbent. Relative selectivity is shown in the equation below:

$$\text{Selectivity }(B)=[\text{vol. percent }C/\text{vol. percent }D]_A/[\text{vol. percent }C/\text{vol. percent }D]_U$$

where C and D are two components of the feed stream represented in volume percent and the subscripts A and U represent the adsorbed and unadsorbed phases, respectively. Thus $C_A$ and $C_U$ represent the concentrations of component C in the adsorbent (adsorbed phase) and feed stream (unadsorbed phase), respectively, and $D_A$ and $D_U$ represent the concentrations of component D in the adsorbent and the feed stream, respectively. Equilibrium conditions are reached when the feed stream passing over a bed of adsorbent does not change composition after contacting the bed of adsorbent. In other words, equilibrium conditions are reached when there is no net transfer of material occurring between the unadsorbed (feed stream) and adsorbed phases (adsorbent).

Where selectivity of two components approaches 1.0, there is no preferential adsorption of one component by the adsorbent with respect to the other; that is, they are both adsorbed (or nonadsorbed) to about the same degree with respect to each other. As the selectivity (B) becomes less than or greater than 1.0, there is a preferential adsorption by the adsorbent for one component with respect to the other. When comparing the selectivity by the adsorbent of one component C over component D, a (B) larger than 1.0 indicates preferential adsorption of component C within the adsorbent. A (B) less than 1.0 would indicate that component D is preferentially adsorbed, leaving an unadsorbed phase richer in component C and an adsorbed phase richer in component D. While separation of an extract component from a raffinate component is theoretically possible when the selectivity of the adsorbent for the extract component with respect to the raffinate component just exceeds a value of 1.0, it is preferred that such selectivity have a value approaching or exceeding 2. The higher the selectivity, the easier the separation is to perform. Higher selectivities permit a smaller amount of adsorbent to be used in the process. Ideally, the desorbent should have a selectivity equal to about 1 or less than 1 with respect to all extract components so that all of the extract components can be extracted as a class and all raffinate components rejected into the raffinate stream.

The selectivity and capacity results of the pulse/dynamic performance evaluation experiments for each formulation in Table 1 are shown in Table 2 below:

TABLE 2

| Formulation | PX/EB Sel | PX/MX Sel | PX/OX Sel | Adsorb. Cap. | PX/PDEB Sel |
|---|---|---|---|---|---|
| A | 1.84 | 5.09 | 4.55 | 11.46 | 1.36 |
| B | 1.84 | 5.32 | 4.75 | 11.08 | 1.39 |
| C | 1.87 | 5.18 | 4.65 | 11.37 | 1.41 |
| D | 1.86 | 5.28 | 4.88 | 10.61 | 1.35 |
| E | 1.80 | 5.12 | 4.59 | 11.34 | 1.28 |
| F | 1.84 | 5.37 | 4.95 | 10.93 | 1.30 |
| G | 1.84 | 5.30 | 4.70 | 11.01 | 1.32 |
| H | 1.84 | 5.42 | 5.03 | 10.51 | 1.30 |
| I | 1.83 | 5.17 | 4.76 | 10.52 | 1.33 |
| J | 1.83 | 5.31 | 4.77 | 10.51 | 1.33 |
| K | 1.84 | 5.20 | 4.70 | 10.58 | 1.29 | where:
PX/EB Sel = para-xylene/ethyl benzene selectivity
PX/MX Sel = para-xylene/meta-xylene selectivity
PX/OX Sel = para-xylene/ortho-xylene selectivity
Adsorb. Cap. = Adsorptive capacity
PX/PDEB Sel = para-xylene/p-diethylbenzene (desorbent) selectivity Based on acceptable data from these experiments, equilibrium SMB process modeling was developed to predict process performance and adsorbent productivity of the binderless BaKX adsorbent in accordance with exemplary embodiments of the present invention. The results of this modeling are shown in FIGS. 3-7. More detailed information about process modeling for calculating productivity is provided in Marco Mazzotti, etc. "Robust Design of Countercurrent Adsorption Separation Processes: 2. Multicomponent Systems", AIChE Journal, November 1994, Vol. 40, No. 11.

Figure 3:
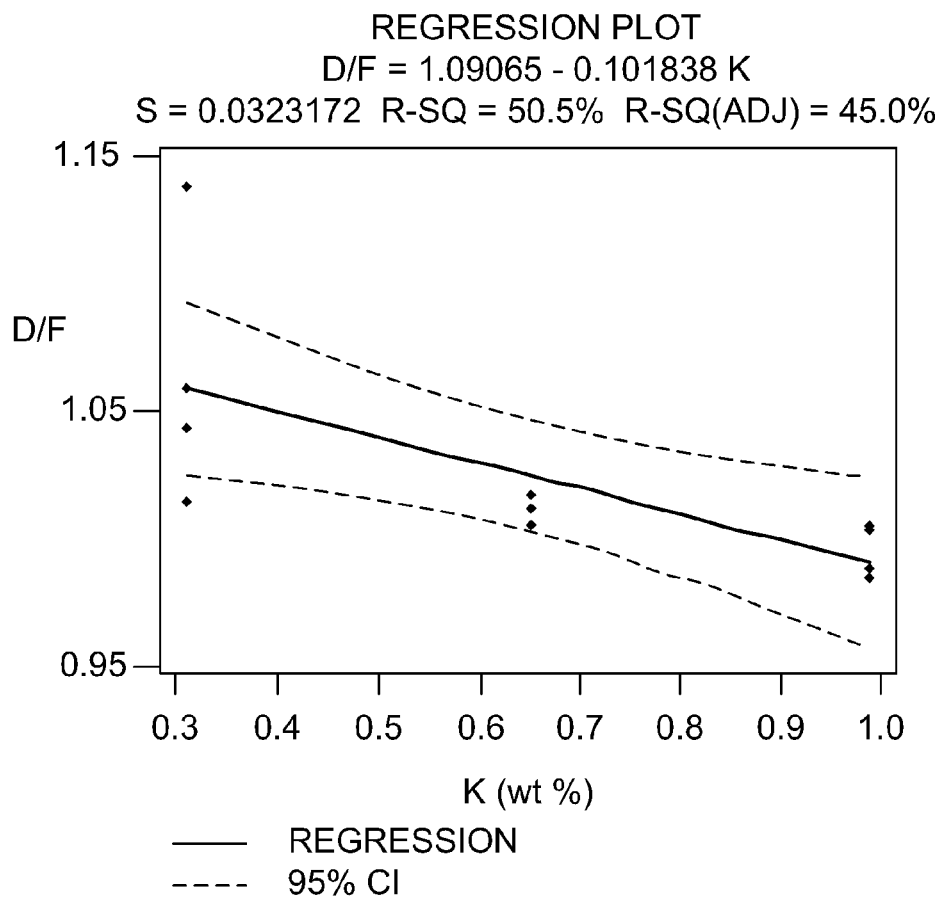
FIG. 3 is a linear regression plot illustrating the relationship between the weight percent of K in a binderless BaKX zeolitic adsorbent in accordance with an embodiment of the present invention and the desorbent/feed (D/F) ratio.

FIG. 3 illustrates the correlation between the level of K in Formulations A-K of the binderless BaKX adsorbent and the desorbent/feed ratio (herein "D/F ratio"). The D/F ratio is an important process parameter that has a strong impact on the operating cost of an adsorptive separation process. The D/F ratio is the ratio of the flow rate of the desorbent to that of the feed stream in the simulated moving bed separation process. The D/F ratio translates into the amount of desorbent required to process a given amount of feed stream. The lowest D/F ratio is preferred. The lower the D/F, the less desorbent is required to displace the adsorbed para-xylene from the adsorbent, i.e., there is a significant reduction of desorbent demand (relative to feed processed). This translates to reduced operating costs, in addition to significantly improving productivity of the adsorptive process. While it is desirable to lower the D/F ratio, it is important that the amount of feed that can be processed not be affected.

As shown in FIG. 3, the D/F ratio was unexpectedly reduced with increasing levels of K, particularly in Formulation C. Formulation C has both high productivity as hereinafter described and low D/F, both important adsorbent characteristics. A Regression/Design of Experiment (DOE) analysis table follows:

The regression equation is:

$$D/F = 1.09065 - 0.101838\, K\,(\text{wt \%})$$

$S=0.0323172$ $R^2=50.5\%$ $R^2(\text{adj})=45.0\%$.
Analysis of Variance:

| Source | DF | SS | MS | F | P |
|---|---|---|---|---|---|
| Regression | 1 | 0.0095911 | 0.0095911 | 9.18338 | 0.014 |
| Error | 9 | 0.0093996 | 0.0010444 | | |
| Total | 10 | 0.0189907 | | | | where:
S=source=indicates the source of variation, either from the factor, the interaction or the error;
$R^2$=regression coefficient;
$R^2(\text{adj})$=regression coefficient (adjusted);
DF=degrees of freedom from each source. If a factor has three levels, the degrees of freedom are 2 (n-1). If there are a total of 30 observations, the degrees of freedom are 29 (n-1);
SS=sum of squares between groups (factor) and the sum of squares within groups (error);
MS=mean squares that are determined by dividing the sum of squares by the degrees of freedom;
F=is calculated by dividing the factor MS by the error MS; and
P=P can be used to determine whether a factor is significant. It is typically compared against an alpha value of 0.05. Therefore, low p-values suggest the predictor is a meaningful addition to the model. This value tests the null hypothesis that the coefficient is equal to zero (no effect). Therefore, when P is <0.05, it means there is less than 5% chance there is no correlation. Here, a value of P<0.05 demonstrates a significant correlation between the D/F ratio and K content. There is >95% confidence that there is a correlation. More detailed background information about the statistical analyses and definitions used herein may be found in "Essentials of SPC in the Process Industries" by James M. Pruett and Helmut Schneider, Instrument Society of America, 1993 and MINITAB Software, by Minitab Inc. 2006.

Figure 4:
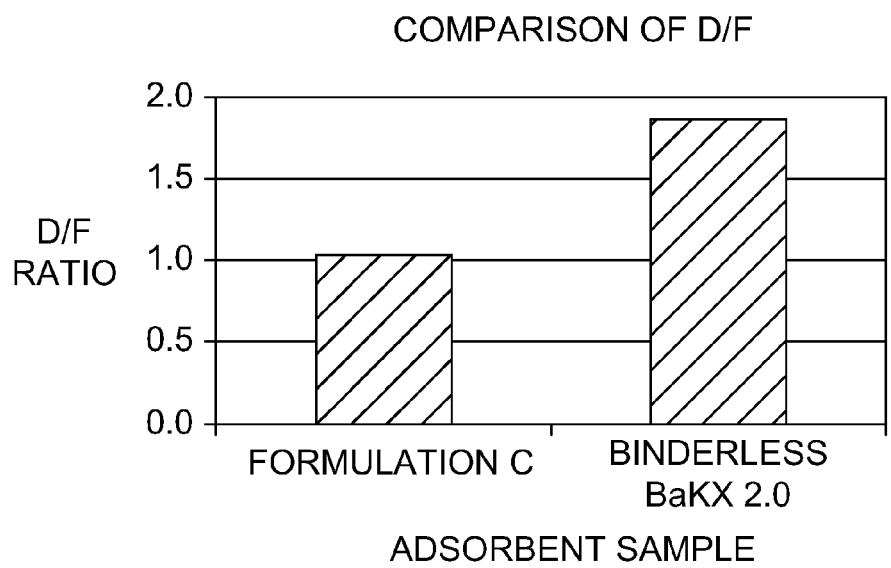
FIG. 4 is a graph comparing the D/F ratio of a binderless BaKX zeolitic adsorbent in accordance with an embodiment of the present invention to the D/F ratio of a binderless BaKX2.0 adsorbent.
Figure 5:
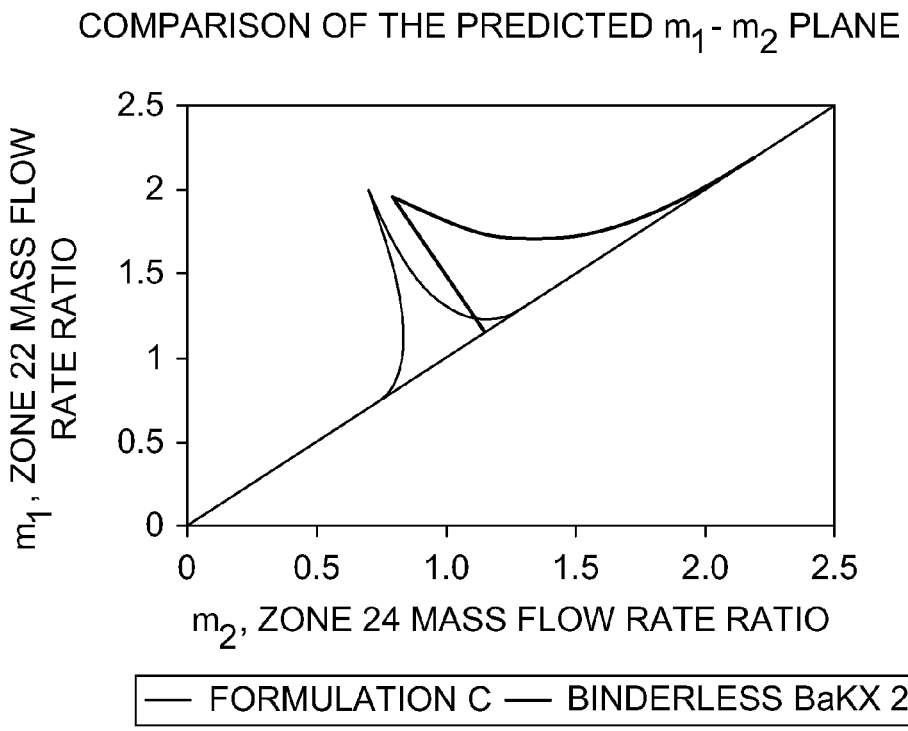
FIG. 5 is a graph comparing the productivity of a binderless BaKX zeolitic adsorbent in accordance with an embodiment of the present invention to the productivity of a binderless BaKX2.0 zeolitic adsorbent.

Referring to FIGS. 4 and 5, respectively, the D/F ratio and productivity of the binderless BaKX zeolitic adsorbent (as represented by Formulation C) was compared with the D/F ratio and productivity of a binderless BaKX2.0 adsorbent prepared by the same method as described above, the 2.0 referring to the silica:alumina molar ratio of the zeolite X in that comparison adsorbent.

As shown in FIG. 4, the D/F ratio of the binderless BaKX adsorbent (referred to in FIG. 3 as "Formulation C") with a silica:alumina molar ratio of 2.5 was calculated to be lower than the D/F ratio of the binderless BaKX2.0 adsorbent (with the silica:alumina molar ratio of 2.0). More specifically, the D/F ratio of the binderless BaKX adsorbent (Formulation C) is shown to be about 1.0 as compared to the D/F ratio of the BaKX2.0 adsorbent of about 1.75. Thus, the amount of desorbent required to process a given amount of feed is less when using the binderless BaKX adsorbent with a silica:alumina molar ratio of 2.5 than when using the binderless BaKX2.0 adsorbent.

FIG. 5 shows the productivity (feed rate) comparison between Formulation C and the binderless BaKX2.0 adsorbent using a predicted $m_1$–$m_2$ plane. The $m_1$–$m_2$ plane represents the feed that can be processed over a fixed bed of the adsorbent in zones 22 and 24 (FIG. 2). The feed flow rate (and thus the productivity) is proportional to $m_1$ (mass flow rate ratio in zone 22)–$m_2$ (mass flow rate ratio in zone 24)) as represented by the equation: $F \propto m_1 - m_2$. The y axis of FIG. 5 represents $m_1$, the mass flow rate ratio (net fluid mass flow rate/adsorbed phase mass flow rate) in zone 22. The x axis of FIG. 5 represents $m_2$, the mass flow rate ratio (net fluid mass flow rate /adsorbed phase mass flow rate) in zone 24. If there is a higher flow rate in zone 22 relative to the flow rate in zone 24, more feed can be processed and the productivity increases. Thus, the higher the difference between $m_1$ and $m_2$, the greater the productivity of the adsorbent, i.e., the more feed can be processed per unit volume of adsorbent under adsorption conditions of about 148-177° Celsius (300-350° Fahrenheit) and a cycle time of 20-34 minutes. Productivity (EQT) is defined as the amount of feed that can be processed per unit volume of adsorbent to achieve 100% para-xylene purity and recovery in the extract. Formulation C with a silica:alumina molar ratio of 2.5 showed a greater than 23% productivity performance advantage over the binderless BaKX2.0 zeolitic adsorbent.

Figure 6:
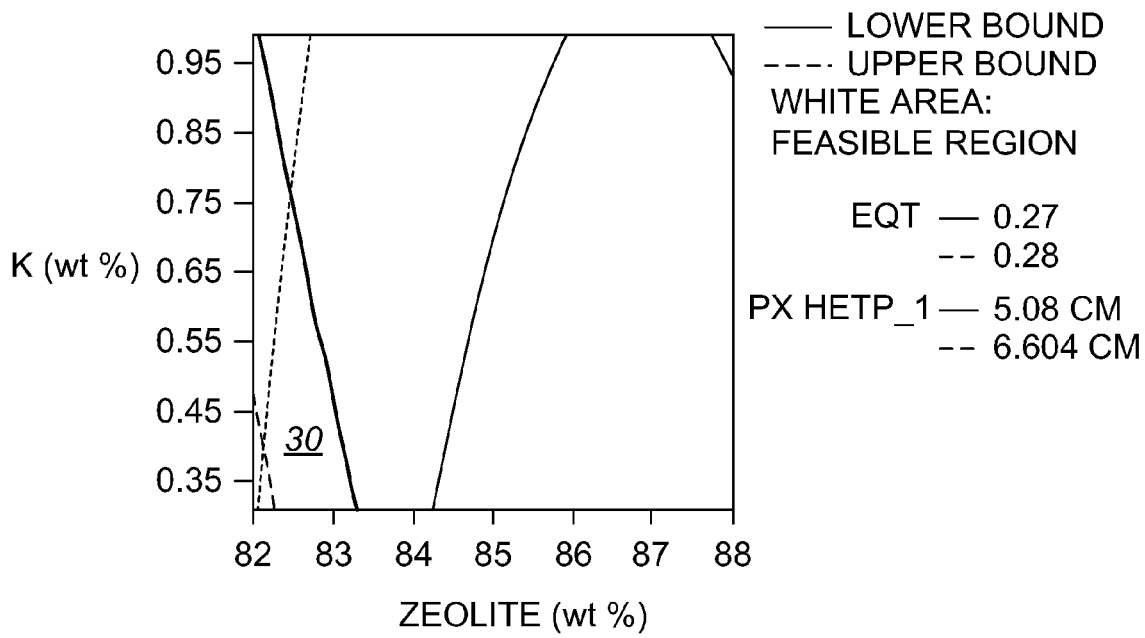
FIG. 6 is an overlaid contour plot illustrating an optimized zeolitic adsorbent formulation region.

The overlaid contour plot of FIG. 6 was constructed by specifying an acceptable range for productivity (EQT), i.e., feed rate based on equilibrium properties, which is to be maximized, of about 0.27 to about 0.28 g/cc, and an acceptable range of PX HETP (Height Equivalent to a Theoretical Plate), which is to be minimized, of about 5.08 cm to about 6.604 cm (2.0 to about 2.6 inches). The definition of the height equivalent to a theoretical plate (HETP) is explained in literature, such as the work by Douglas Ruthven in "Principles of Adsorption and Adsorption Processes" (John Wiley & Sons, Inc., 1984). It is used to estimate and compare the mass transfer rate of different adsorbents. A lower HETP value means a better mass transfer rate. Therefore, the performance advantage of an adsorbent with a low HETP value will be maintained when the SMB process is operated at a shorter cycle time. Still referring to FIG. 6, the region 30 is the feasible region in terms of the two factors or variables, K level (wt %) and wt % of Zeolite X. The third factor, or variable, cornstarch level, was set at a fixed level, and in FIG. 6, cornstarch level was set at its highest level (5%). The region 30 in FIG. 6 is where the two variables of weight percent of K level and Zeolite X overlap. This region represents the optimized binderless BaKX zeolitic adsorbent formulations that result in simultaneous high values of productivity and mass transfer rates. It can be seen that Formulation C (from Table 1) falls closest to this region.

Figure 7:
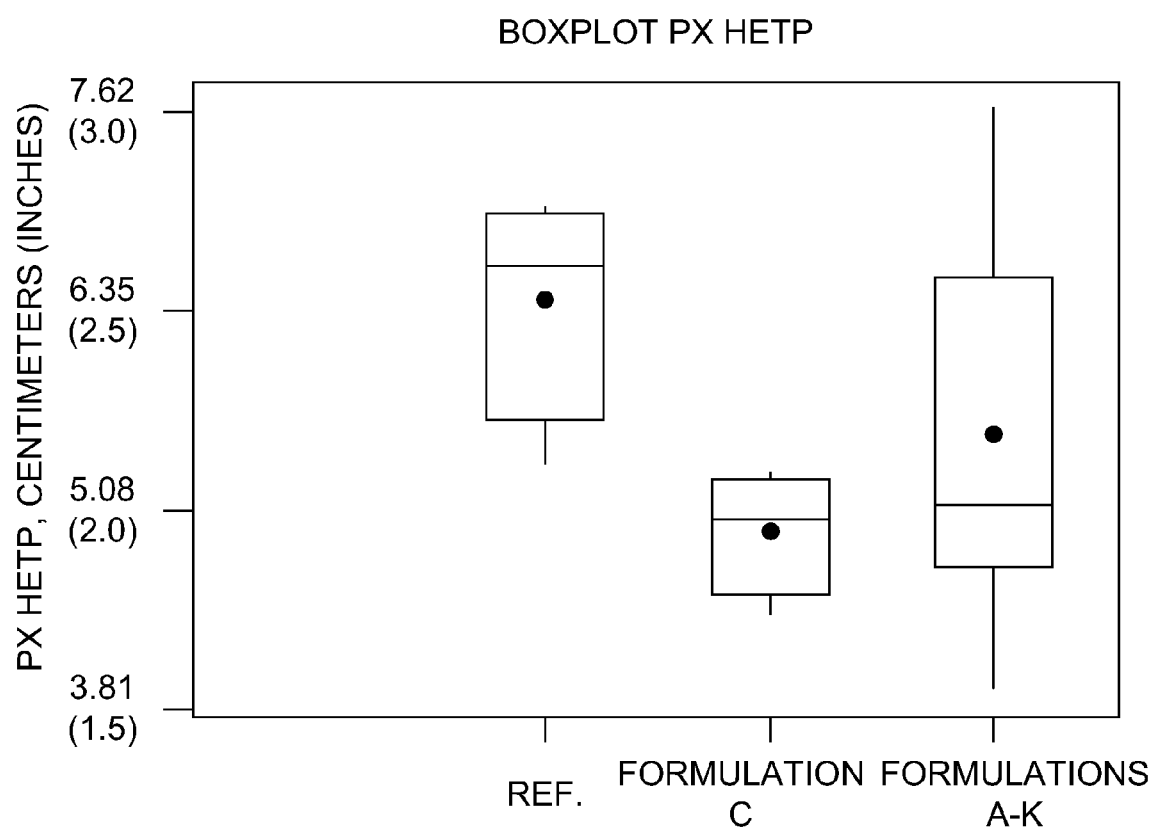
FIG. 7 is a box plot illustrating the relative mass transfer rates of different adsorbents including the binderless BaKX zeolitic adsorbent in accordance with an embodiment of the present invention.

Referring to FIG. 7, the mass transfer rate of various adsorbents was assessed by conducting PX HETP analysis of pulse/dynamic test results. The adsorbents assessed included a reference non-binderless zeolitic adsorbent that is commercially available for use in liquid phase adsorptive separation processes (referred to in FIG. 7 as "Ref"), Formulation C (Table 1) of the binderless BaKX adsorbent which was tested multiple times for purposes of analysis, as well as all Formulations A-K collectively. Box plot analysis of the mass transfer rates (HETP) shows that the median mass transfer rate of Formulation C of the binderless BaKX adsorbent is substantially equal to the median mass transfer rate of Formulations A-K (tested collectively) and lower than the median mass transfer rate of the reference commercially available non-binderless zeolitic adsorbent. The mean mass transfer rate of Formulation C was lower than the mean mass transfer rates of both the reference adsorbent and Formulations A-K collectively. The mean mass transfer rates are identified with a dot.

Figure 8:
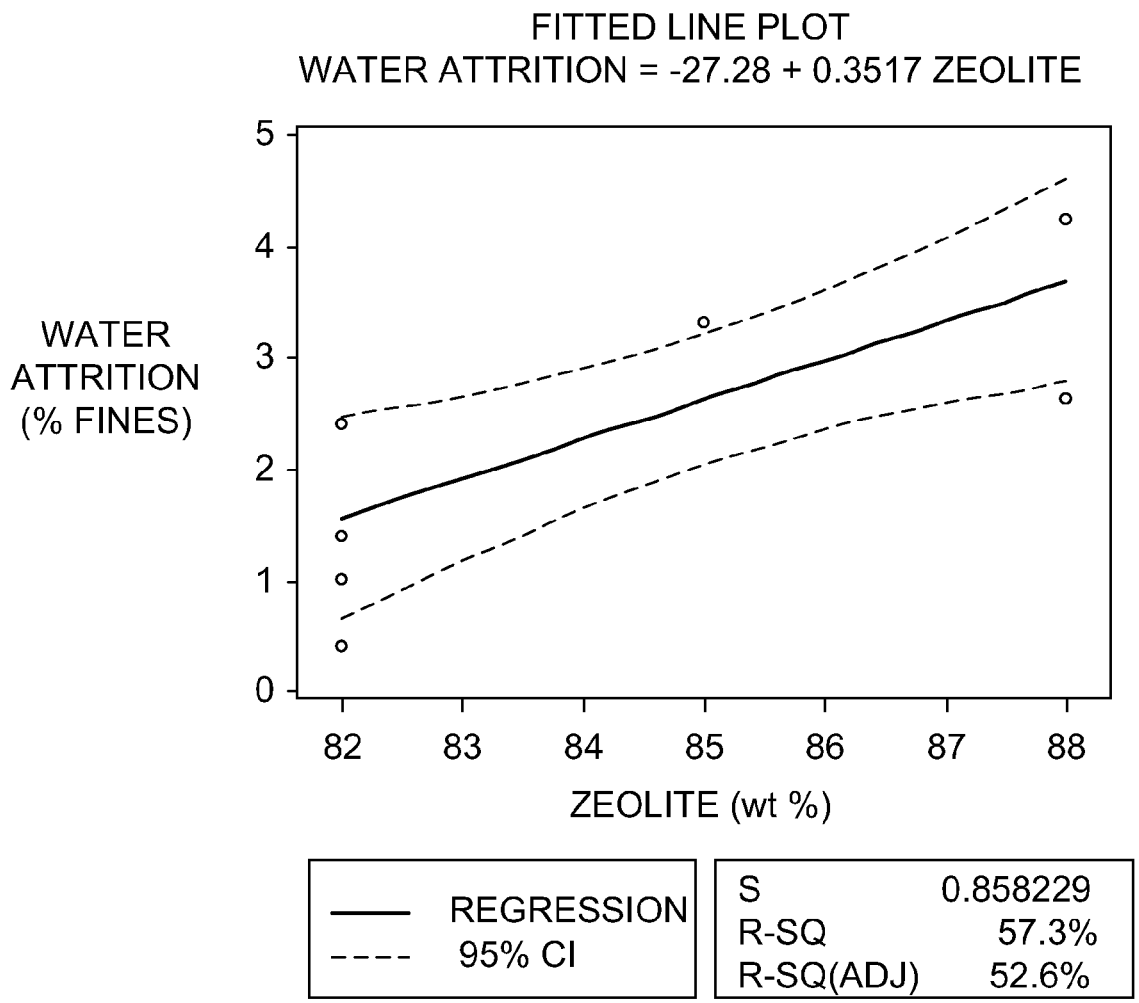
FIG. 8 is a linear regression plot of water attrition loss (% fines) versus Zeolite X (wt %) in the binderless BaKX zeolitic adsorbents in accordance with an embodiment of the present invention.

FIG. 8 illustrates the correlation between attrition of the adsorbent (as measured by % of adsorbent fines) and the wt % of zeolite X of Formulations A-K of the binderless BaKX adsorbent. To investigate attrition of the binderless BaKX zeolitic adsorbent according to exemplary embodiments of the present invention, a laboratory scale attrition test was performed. The attrition of the adsorbent and subsequent release of fines during filtration was assessed. The lower the percentage of fines, the lower the attrition of the adsorbent. This test involved submerging the binderless BaKX zeolitic adsorbent in water on a shake table. The water and adsorbent were shaken at ambient temperature and pressure for about 30 minutes. After shaking, the water including fines was removed from the adsorbent by filtration. The fines collected were dried and weighed to determine the percentage of fines generated, represented on the y axis of FIG. 8. Water attrition loss corresponds to the mechanical strength of the adsorbent. Attrition arises from a lack of mechanical strength. Loss of the adsorbent through attrition results in increased operating costs and shorted adsorbent life.

The results of the attrition test are shown in FIG. 8. The regression equation was:

water attrition=−27.28+0.3517% of Zeolite X $S=0.858229$ $R^2=57.3\%$ $R^2$ (adj)=52.6%.

Analysis of Variance:

| Source | DF | SS | MS | F | P |
| --- | --- | --- | --- | --- | --- |
| Regression | 1 | 8.9042 | 8.90420 | 12.09 | 0.007 |
| Error | 9 | 6.6290 | 0.73656 | | |
| Total | 10 | 15.5332 | | | |

The value of P demonstrates a significant correlation between water attrition and zeolite X content. There is >95% confidence that there is a correlation.

The attrition results show that as the weight percentage of zeolite X in the binderless BaKX zeolitic adsorbent increased, the attrition loss increased. Stated another way, as the kaolin clay binder level in the binderless BaKX zeolitic adsorbent increased from 10% to 20%, the attrition loss decreased, thereby indicating increased mechanical strength of the adsorbent as the amount of binder increased. With increased mechanical strength, the life of the adsorbent is increased resulting in lower capital and operating costs, as well as stable process operations. Thus, the binderless BaKX zeolitic adsorbent with a lower wt % of zeolite X and a higher percentage of binder-converted zeolite (from the conversion of kaolin clay binder) is more resistant to attrition.

Figure 9:
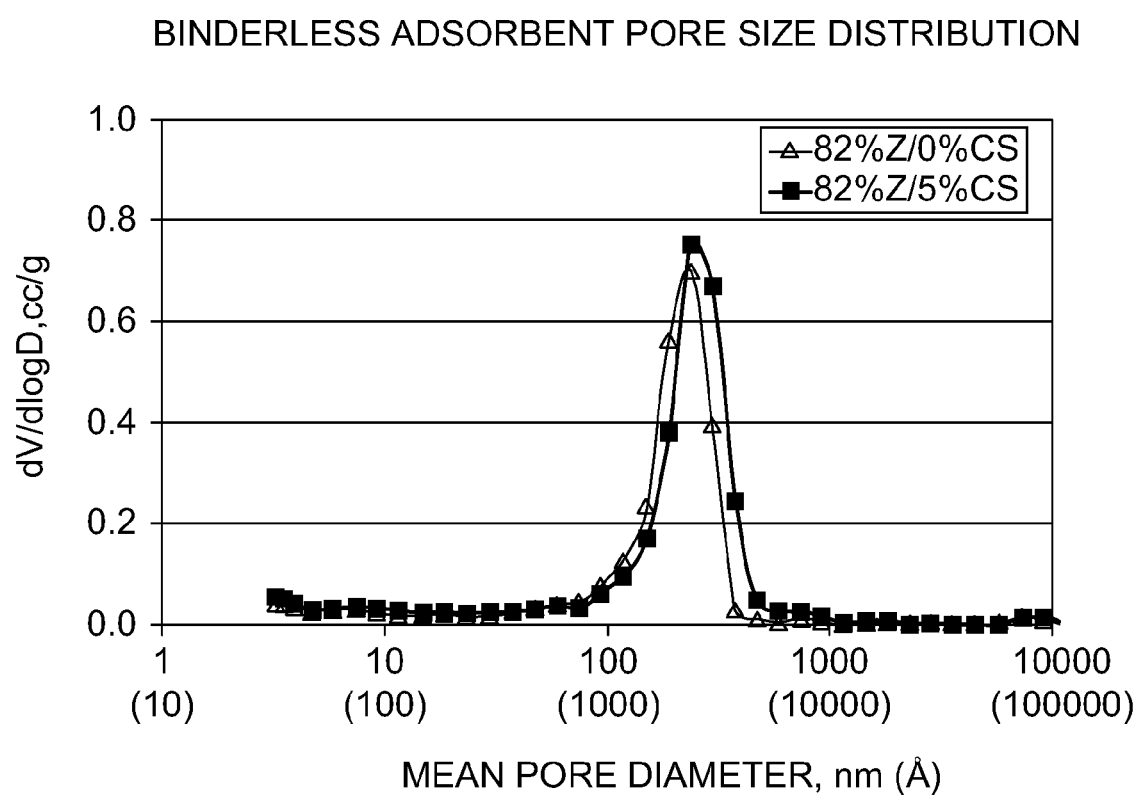
FIG. 9 is a plot of mercury porosimetry results on a binderless BaKX zeolitic adsorbent prepared with cornstarch in accordance with exemplary embodiments of the present invention and without cornstarch.

Pore volume measurements and mean pore size measurements were made via the mercury intrusion porosimetry method as described in UOP Test Method No. UOP578-02 (available through ASTM International, 100 Barr Harbor Drive, PO Box C700, West Conshohocken, Pa., 19428-2959 USA). Mercury Intrusion Porosimetry measures meso-pores and macro-pores, but not micro-pores. The binderless adsorbent prepared with 82% zeolite (Z)/5% cornstarch (CS) (Formulation C) and a binderless BaKX adsorbent prepared with 82% zeolite (Z) without cornstarch (Formulation A) were subjected to increasing hydraulic pressure on a volume of mercury in the penetrometer, which also contained the adsorbent. As the pressure was increased on the mercury, the mercury began to intrude or penetrate into the pores of the adsorbent, the largest pores filling first at the lowest pressure. As the pressure ramped from slightly above atmospheric to a maximum of 413,688 kPa (60,000 psi), data regarding the mercury intruded versus pressure was collected. The pressure was converted into equivalent cylindrical pore diameter and the total mercury volume intruded in a specific range was converted into the total pore volume, the mean being the mean pore diameter. The results are shown in FIG. 9. Formulation C with cornstarch showed a total pore volume of about 0.29 cc/g while Formulation A without cornstarch showed a lower total pore volume of 0.25 cc/g. FIG. 9 also shows a larger volume of meso- and macro-pores in the adsorbent with cornstarch as compared with those in the adsorbent without cornstarch. About 11% of the pore volume is from meso-pores and about 89% of the pore volume is from macro-pores. The mean pore diameter in the adsorbent with cornstarch is about 166 nm, which is greater than the mean pore diameter in the adsorbent without cornstarch (164 nm). The higher pore volume (higher porosity) and larger pore size will result in a faster mass transfer rate. The X axis is in log form so as to reduce the length of the x axis.

From the foregoing, it is to be appreciated that the exemplary embodiments of the binderless BaKX zeolitic adsorbent described herein increase the productivity of the adsorptive separation process and decrease operating costs by using less adsorbent and less desorbent. The adsorbent requires less desorbent circulation per ton of product compared to prior art adsorbents. Lower desorbent circulation means lower utility consumption per ton of product. Higher productivity means more para-xylene can be produced with a fixed adsorbent volume. In addition, the binderless BaKX zeolitic adsorbent shows better mass transfer properties and mechanical strength.

While at least one exemplary embodiment has been presented in the foregoing detailed description of the invention, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing an exemplary embodiment of the invention, it being understood that various changes may be made in the function and arrangement of elements described in an exemplary embodiment without departing from the scope of the invention as set forth in the appended claims and their legal equivalents.

What is claimed is:

1. A binderless BaKX zeolitic adsorbent comprising:
   a binder-converted zeolite portion formed from x wt % inert clay binder, wherein x is in the range of about 10 to about 20% by weight of the binderless BaKX zeolitic adsorbent;
   (100-x) wt % Zeolite X with a silica: alumina molar ratio of about 2.5±0.5; and
   barium (Ba) and potassium (K) at cationic exchangeable sites within the binderless BaKX zeolitic adsorbent, wherein K is in the range of about 0.25 to about 0.9% by weight and the Ba is greater than about 31.6% by weight of the binderless BaKX zeolitic adsorbent; and wherein a total pore volume of the binderless BaKX zeolitic adsorbent measured by Hg intrusion porosimetry is between 0.25 cc/g and 0.35 cc/g.

2. The binderless BaKX zeolitic adsorbent of claim 1, wherein the inert clay binder and Zeolite X are mixed with cornstarch prior to formation of the binder-converted zeolite portion, the cornstarch comprising up to about 5% by weight of the combined weight percent of the binder-converted zeolite portion and the Zeolite X, the cornstarch dissipating prior to formation of the binder-converted zeolite portion.

3. The binderless BaKX zeolitic adsorbent of claim 2, wherein in weight percentages of the binderless BaKX zeolitic adsorbent, Zeolite X comprises about 82%, the binder-converted zeolite comprises about 18%, the Ba comprises about 33%, the K comprises about 0.3%, and Na comprises about 0.11%.

4. The binderless BaKX zeolitic adsorbent of claim 3, wherein cornstarch comprising 5% by weight of the combined weight percent of the binder-converted zeolite portion and the Zeolite X was mixed with the Zeolite X and inert clay binder.

5. The binderless BaKX zeolitic adsorbent of claim 1, wherein the inert clay binder comprises kaolin clay.

6. The binderless BaKX zeolitic adsorbent of claim 1, wherein the Zeolite X has a silica: alumina molar ratio of about 2.5.

7. The binderless BaKX zeolitic adsorbent of claim 1, wherein the binder-converted zeolite portion has a silica: alumina molar ratio of from about 2.0 to about 2.2.

8. The binderless BaKX zeolitic adsorbent of claim 1, wherein Na at cationic exchangeable sites within the binderless BaKX zeolitic adsorbent is less than about 0.3% by weight of the binderless BaKX zeolitic adsorbent.

9. The binderless BaKX zeolitic adsorbent of claim 1, wherein LOI at 900° C. comprises about 4 to about 7 wt %.

10. The binderless BaKX zeolitic adsorbent of claim 1, wherein a majority of the total pore volume of the binderless BaKX zeolitic adsorbent is from pores sized greater than 50 nm.

* * * * *